(12) United States Patent
Hibner

(10) Patent No.: US 7,491,177 B2
(45) Date of Patent: Feb. 17, 2009

(54) BIOPSY NEEDLE AND METHOD

(75) Inventor: John A. Hibner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 234 days.

(21) Appl. No.: 11/346,716

(22) Filed: Feb. 3, 2006

(65) Prior Publication Data

US 2007/0185411 A1    Aug. 9, 2007

(51) Int. Cl.
*A61B 10/00* (2006.01)

(52) U.S. Cl. .................................... 600/566

(58) Field of Classification Search ............ 600/562, 600/564–568; 604/116; 606/116; 52/285.1; 160/135, 381; 403/103, 171, 231
See application file for complete search history.

(56) References Cited

U.S. PATENT DOCUMENTS

| | | | |
|---|---|---|---|
| 5,526,822 A | 6/1996 | Burbank et al. | |
| 5,878,802 A * | 3/1999 | Richter et al. | ............... 160/135 |
| 5,895,401 A | 4/1999 | Daum et al. | |
| 6,077,230 A | 6/2000 | Gregoire et al. | |
| 6,086,544 A | 7/2000 | Hibner et al. | |
| 6,605,047 B2 * | 8/2003 | Zarins et al. | ................. 600/562 |
| 6,620,111 B2 | 9/2003 | Stephens et al. | |
| 6,626,849 B2 | 9/2003 | Huitema et al. | |
| 6,638,235 B2 | 10/2003 | Miller et al. | |
| 6,981,949 B2 * | 1/2006 | Hibner et al. | ............... 600/566 |
| 2002/0029007 A1 | 3/2002 | Bryan et al. | |
| 2003/0109803 A1 * | 6/2003 | Huitema et al. | ............. 600/564 |
| 2003/0199753 A1 | 10/2003 | Hibner et al. | |
| 2003/0199785 A1 | 10/2003 | Hibner et al. | |
| 2006/0074343 A1 * | 4/2006 | Hibner | ....................... 600/566 |
| 2006/0074345 A1 | 4/2006 | Hibner | |

FOREIGN PATENT DOCUMENTS

EP         1642533         4/2006

OTHER PUBLICATIONS

European Search Report, dated Jun. 19, 2007 for EPO Application No. EP 07250439.2.
European Search Report, dated Jun. 19, 2007 for EPO Application No. 07250439.2.

* cited by examiner

*Primary Examiner*—Max Hindenburg
*Assistant Examiner*—Brian Szmal
(74) *Attorney, Agent, or Firm*—Frost Brown Todd LLC

(57) ABSTRACT

A biopsy needle, where at least a portion thereof is configured from a non-ferrous and/or non-conductive material that reduces or eliminates MRI artifact while retaining desirable levels of strength and the ability to resist significant bending loads.

7 Claims, 7 Drawing Sheets

BIOPSY NEEDLE AND METHOD

FIELD OF THE INVENTION

The present invention is related generally to biopsy devices and, more particularly, to a needle assembly for use with a biopsy device for acquiring a tissue sample.

BACKGROUND OF THE INVENTION

The diagnosis and treatment of patients with cancerous tumors, pre-malignant conditions, and other disorders has long been an area of intense investigation. Non-invasive methods for examining tissue include palpation, thermography, PET, SPECT, Nuclear imaging, X-ray, MRI, CT, and ultrasound imaging. When the physician suspects that tissue may contain cancerous cells, a biopsy is generally done either in an open procedure or in a percutaneous procedure. For an open procedure, a scalpel is used by the surgeon to create a large incision in the tissue in order to provide direct viewing and access to the tissue mass of interest. Removal of the entire mass (excisional biopsy) or a part of the mass (incisional biopsy) is performed. For a percutaneous biopsy, a needle-like instrument is inserted through a very small incision to access the tissue mass of interest and to obtain a tissue sample for later examination and analysis.

The advantages of the percutaneous method as compared to the open method are significant: less recovery time for the patient, less pain, less surgical time, lower cost, less risk of injury to adjacent bodily tissues such as nerves, and less disfigurement of the patient's anatomy.

Generally, there are two ways to percutaneously obtain a portion of tissue from within the body: aspiration and core sampling. Aspiration of the tissue through a fine needle requires the tissue to be fragmented into pieces small enough to be withdrawn in a fluid medium. This method is less intrusive than other known sampling techniques, but one may only examine cells in the liquid (cytology) and not the cells and the structure (pathology). In core sampling, a core or fragment of tissue is obtained for histologic examination and/or genetic tests, which may be done via a frozen or paraffin section. The type of biopsy used depends mainly on various factors present in the patient, and no single procedure is ideal for all cases. However, core biopsies seem to be more widely used by physicians.

The following patent documents are incorporated herein by reference for the purpose of illustrating biopsy devices and methods and, to no extent, limit the scope of the invention: U.S. Pat. No. 5,526,822 issued Jun. 18, 1996; U.S. Pat. No. 5,895,401 issued Apr. 20, 1999; U.S. Pat. No. 6,086,544 issued Jul. 11, 2000; U.S. Pat. No. 6,620,111 issued Sep. 16, 2003; U.S. Pat. No. 6,626,849 issued Sep. 30, 2003; U.S. Pat. No. 6,638,235 issued Oct. 28, 2003; US Patent Application 2003/0109803 published Jun. 12, 2003; US Patent Application 2003/0199753 published Oct. 23, 2003; US Patent Application 2003/0199754 published Oct. 23, 2003; US Patent Application 2003/0199785 published Oct. 23, 2003; and U.S. Ser. No. 08/825,899 filed on Apr. 2, 1997.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The use of a double lumen biopsy needle incorporating vacuum suction to obtain a tissue sample is known in the art. With devices of this type, the needle is inserted into a small incision in a patient and is advanced through tissue until the needle is adjacent the tissue of interest. At that point, a vacuum source may be activated, providing suction inside one of the two lumens. The suction is communicated to the second lumen via a passage between the two lumens. The second lumen may contain an aperture through which suspicious tissue may be drawn when the vacuum source is activated. Once tissue is drawn into the aperture, the surgeon may advance a cutter through the second lumen in order to excise a sample from the tissue of interest.

While biopsy needles of the type described above are useful in obtaining tissue samples, such needles often generate MRI artifact or present a projectile hazard due to the materials, such as iron, used in their construction. MRI artifact may obfuscate a patient's true condition and may diminish the precision with which tissue samples are removed. Attempts to construct biopsy needles producing a reduced MRI artifact have been made. However, such biopsy needles may suffer in other categories, such as the ability to withstand significant bending loads, due to the limited number of materials from which a biopsy needle may be constructed and still generate little or no MRI artifact.

Additionally, current biopsy needle construction generally involves the welding of components in multiple steps to assemble a complete instrument. Increasing the number of components required for assembly may consequently increase both the manufacturing cost and assembly cost for the instrument. The manufacturing cost may increase due to an increased number of parts that must be designed and constructed and the assembly cost may increase due to the use of a time-consuming welding process that is applied to multiple components.

Accordingly, it would be advantageous to provide a biopsy needle that creates little or no MRI artifact and is non-conductive while still retaining the desirable properties of strength and durability. It would be further advantageous to provide a cost-effective biopsy needle that is easily assembled from a minimal number of components.

SUMMARY OF THE INVENTION

Disclosed is a biopsy device having a handle with a needle assembly attached thereto. In one version, the needle assembly includes an exterior surface configured from a non-ferrous and/or non-conductive material that has a tissue-receiving aperture configured therein. The needle assembly further includes an insert constructed from a non-ferrous and/or non-conductive material that is coupled with the exterior surface, where the insert may be configured to divide at least a portion of the lumen defined by the exterior surface into a vacuum lumen and a cutter lumen. The needle assembly further includes a cutter, where the cutter is operably configured to translate within the cutter lumen to sever tissue retained within the tissue receiving aperture. The insert may be coupled with the exterior surface by pushing the insert into a distal opening in the exterior surface.

BRIEF DESCRIPTION OF THE DRAWINGS

The novel features and steps of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
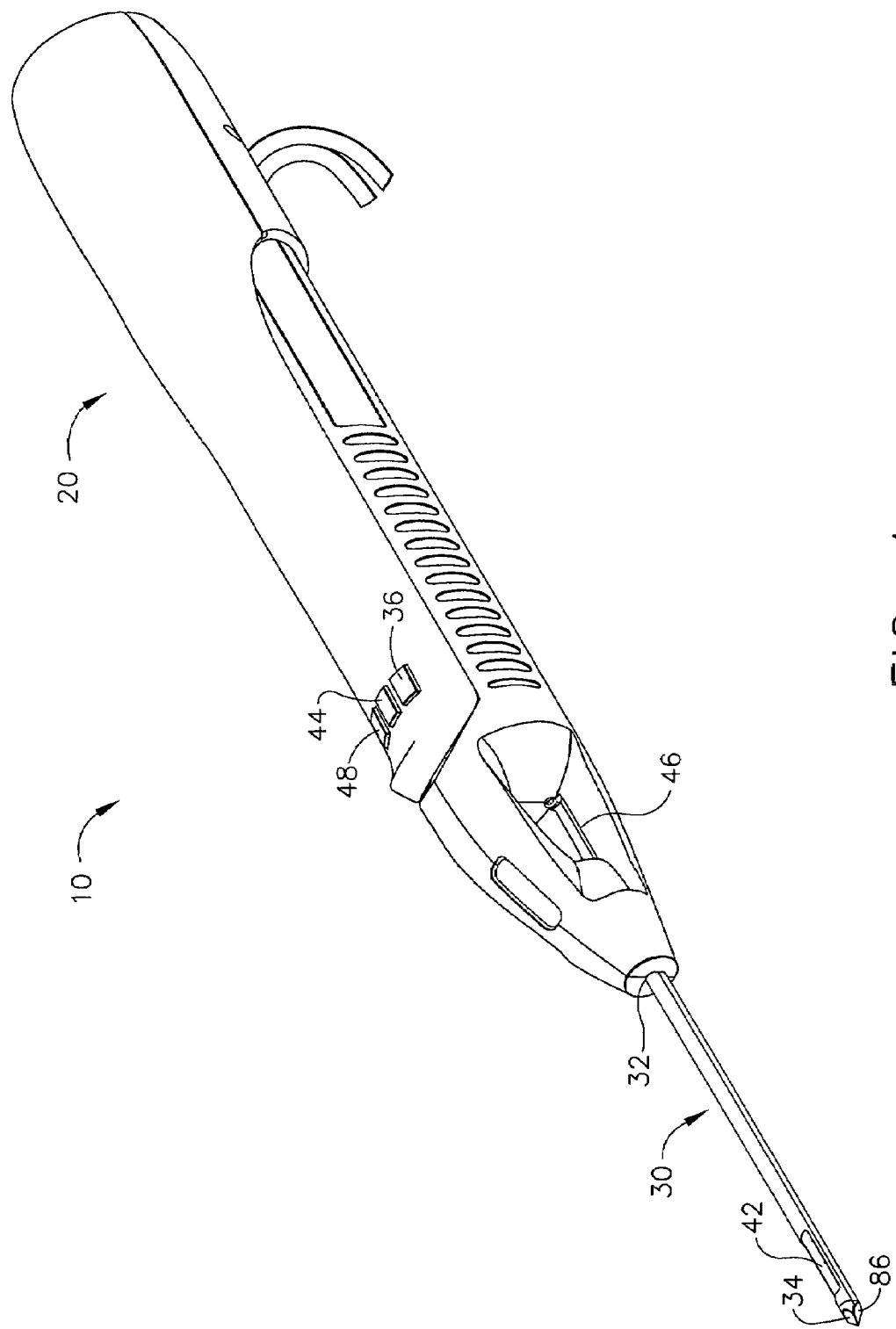
FIG. 1 is an isometric view of one version of a hand-held vacuum-assisted biopsy device.

FIG. 1 shows one version of a biopsy device 10, which may be hand-held and/or vacuum assisted, having a handle 20 detachably or permanently connected to a needle assembly 30 having a proximal portion 32 and a distal portion 34. Together, in one version, they constitute a lightweight, ergonomically-shaped, hand-manipulated biopsy device 10. In one aspect, the needle assembly 30 may be part of a disposable probe that may mount on the handle 20. The biopsy device 10 may be used in conjunction with an MRI to guide the needle assembly 30. Since the handle 20 may be manipulated by the operator's hand, the operator may steer the needle assembly 30 with great freedom towards the tissue mass of interest. The surgeon has tactile feedback while doing so and may therefore ascertain to a significant degree the density and hardness of the tissue being encountered. In addition, the handle 20 may be held approximately parallel to the chest wall of a patient for obtaining tissue portions closer to the chest wall than may be obtained when the needle assembly 30 is attached to another type of device. Alternatively, the needle assembly 30 may be attached to an electromechanical arm, a platform, a table or other suitable support. Such alternative mountings may be used in conjunction with applications in which the needle assembly 30 is guided by stereotactic (x-ray) or MRI modalities.

Still referring to FIG. 1, as controls for obtaining a tissue sample, handle 20 may include a forward button 36 which may be used to move a cutter 38 (FIG. 4) distally through a cutter lumen 40 to sever a sample of targeted tissue collected in a tissue-receiving port 42. Handle 20 may further include a reverse button 44 which may be used to move the cutter 38 proximally through the cutter lumen 40, thereby moving the tissue sample in the tissue-receiving port 42 to a tissue collection site 46. A vacuum button 48 on the handle 20 may be used to open or close a first vacuum line (not shown) for communicating suction to a vacuum lumen 52 so as to cause tissue to become disposed within the tissue-receiving port 42 and a second vacuum line (not shown) for communicating axial suction to the cutter 38 to aid in withdrawal of a severed tissue sample. It will be appreciated that the handle 20 is disclosed by way of example only, where it is contemplated that versions of the present invention may be used with any suitable biopsy device.

Figure 2:
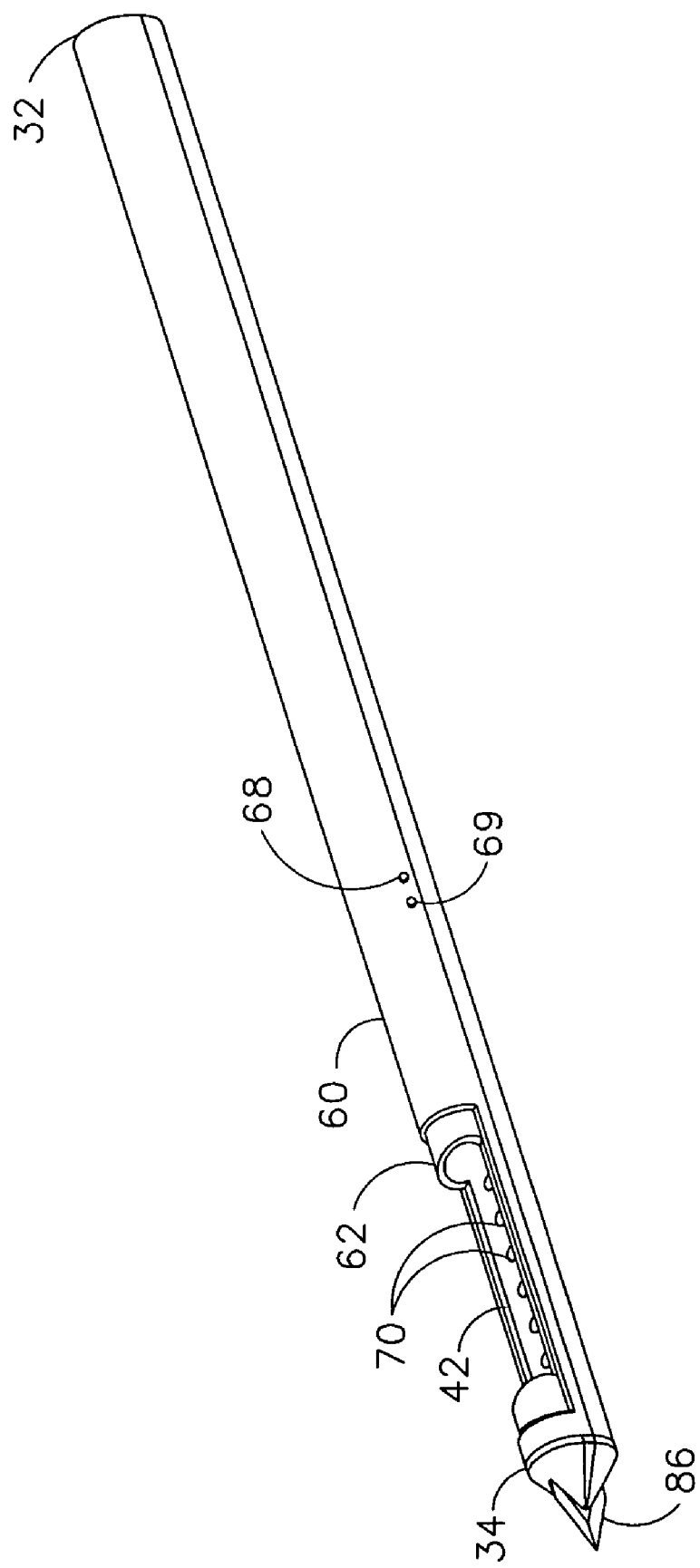
FIG. 2 is a more detailed side view of a needle assembly shown in FIG. 1.
Figure 3:
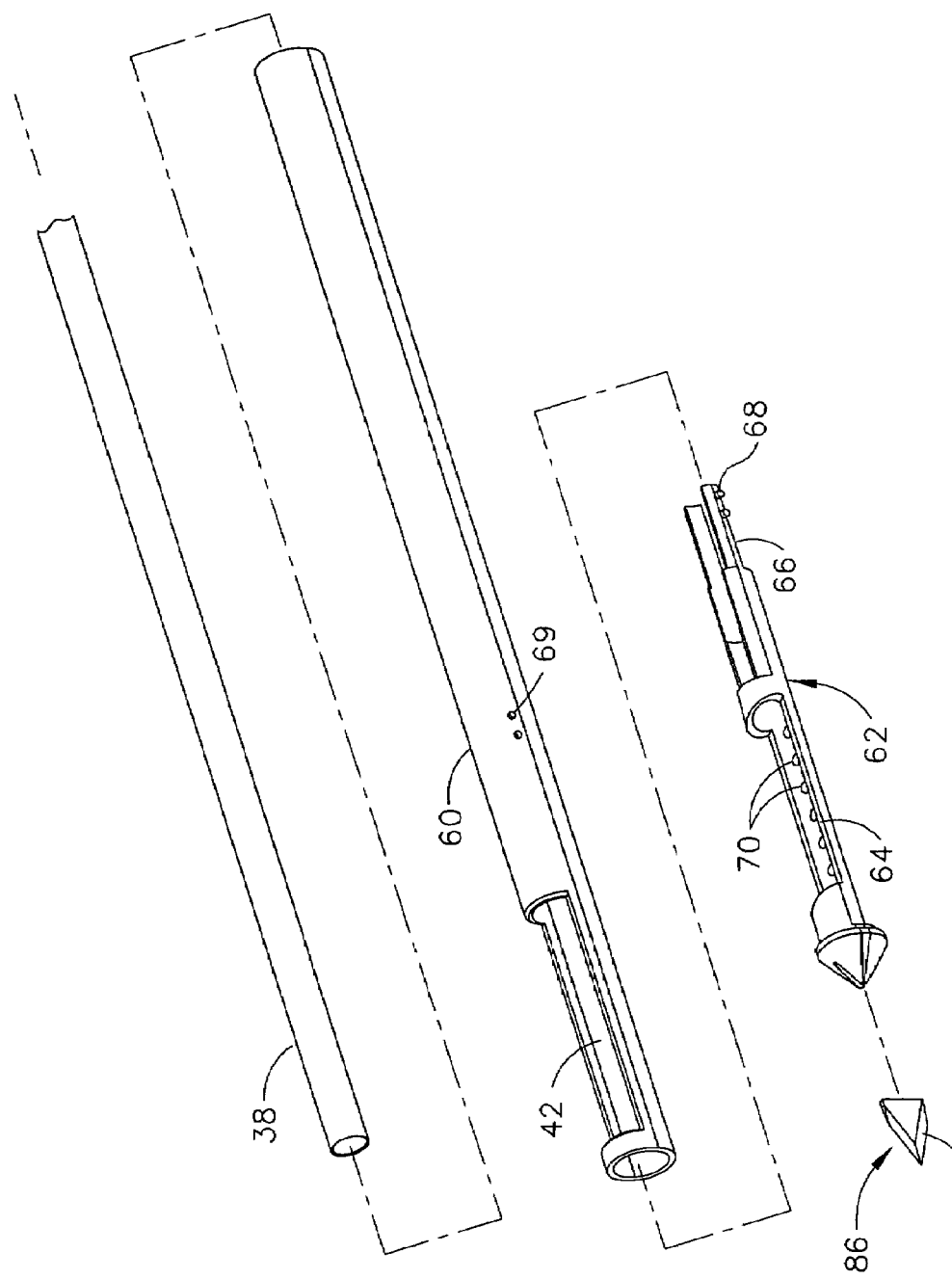
FIG. 3 is an exploded view of the needle assembly shown in FIG. 1.
Figure 4:
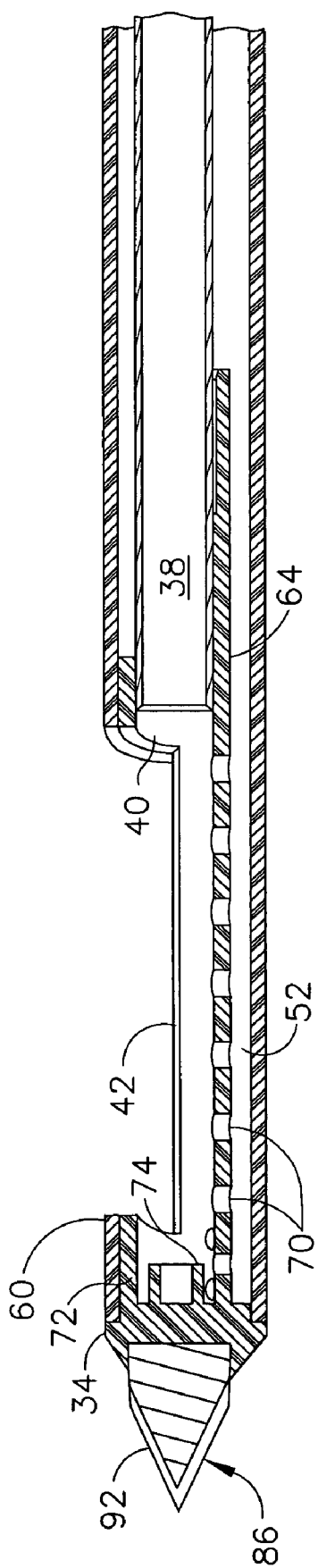
FIG. 4 is a longitudinal cross-section view of the needle assembly shown in FIG. 2.
Figure 5:
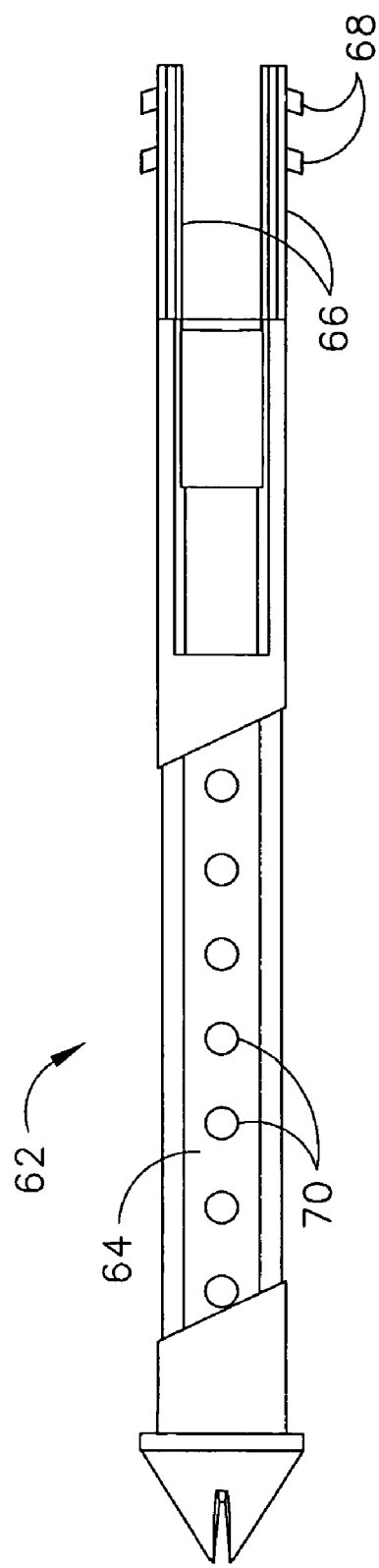
FIG. 5 is a top view of the an insert of the needle assembly shown in FIG. 3.
Figure 6:
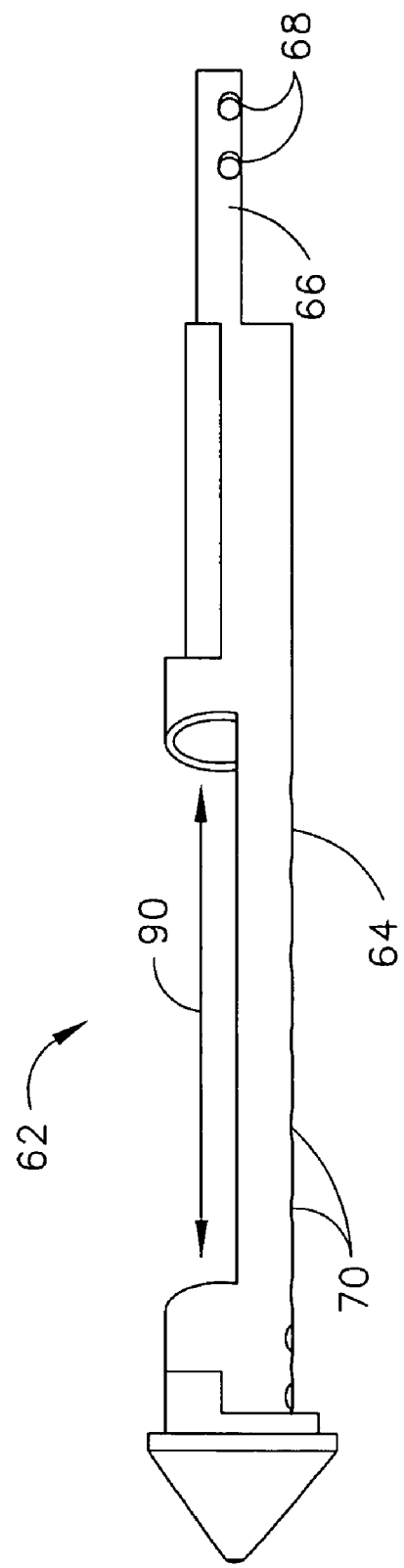
FIG. 6 is a left side view of the insert shown in FIG. 3.
Figure 7:
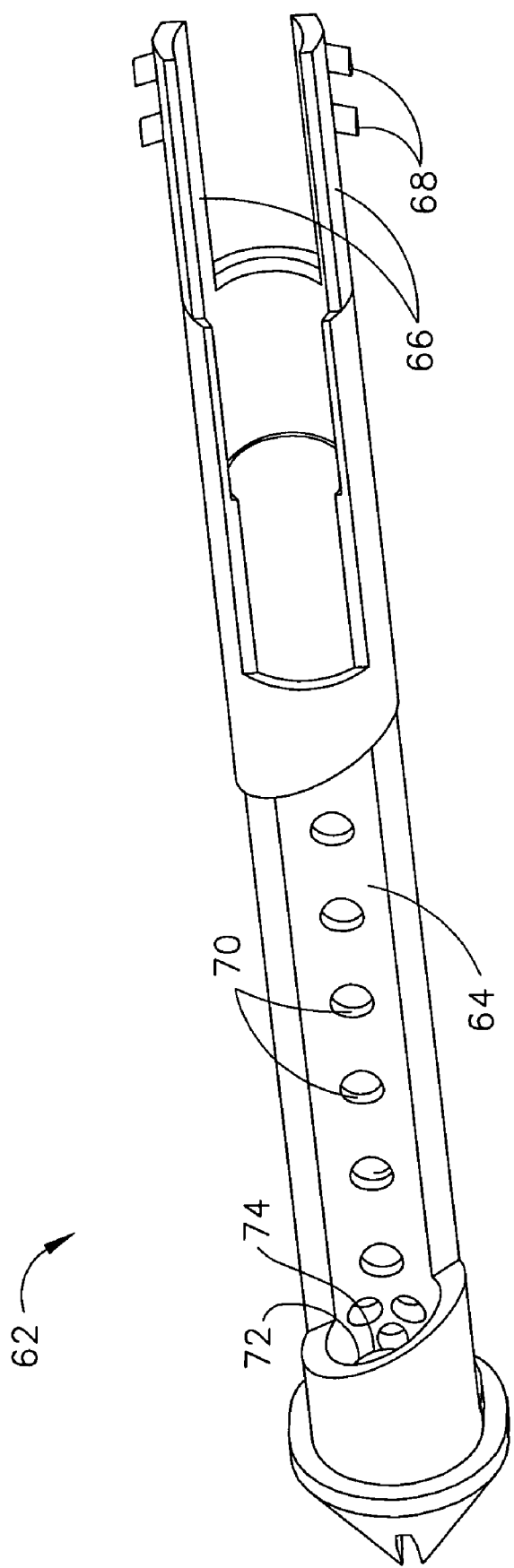
FIG. 7 is an isometric view of the insert shown in FIG. 3.

Referring, in particular, to FIGS. 2-4, the needle assembly 30 includes an exterior surface 60 coupled with an insert 62. The exterior surface 60 may be, for example, an oval or circular tube, cannula, lumen or the like configured from any suitable non-ferrous material, such as a woven carbon composite, a material marketed under the trademark VECTRA held by General Electric, a New York corporation, and/or a material marketed under the trademark ULTEM, held by Celanese, a Delaware corporation, and may be adapted to receive the insert 62 into the distal end thereof. Configuring the exterior surface 60 from a non-ferrous material may reduce or eliminate MRI artifact that may obfuscate a patient's true condition and/or diminish the precision with which tissue samples are removed. Additionally, a non-ferrous and non-conductive material, such as Ultem or Vectra, may be selected that reduces or eliminates the projectile hazard that may be caused by magnetically reactive materials. In one version, the non-ferrous material from which the exterior surface 60 is configured is a woven carbon composite material, where the use of such a woven material may reduce or eliminate MRI artifact while preserving the ability of the biopsy device 10 to, for example, withstand significant bending loads. It will be appreciated that the exterior surface 60 or any other suitable component of the biopsy device 10 may be configured from a non-ferrous material, a non-conductive material, an inert material, Ultem, Vectra, a carbon composite, and/or woven carbon composite to provide advantageous strength while reducing or eliminating MRI artifact and/or a projectile hazard.

Referring, in particular, to FIGS. 4-7, the insert 62 may be a molded polymeric component adapted for insertion and retention within the distal end of the exterior surface 60. In one aspect, a tissue-piercing tip 86, having a proximal portion and a distal portion, may be disposed on the distal end of the insert 62 to provide the initial incision into the patient. The distal portion of the tissue-piercing tip 86 may include a cutting edge 92 of sufficient sharpness to cut through human tissue and thereby aid in moving the needle assembly 30 adjacent the tissue of interest. The junction of the tissue-piercing tip 86 and the insert 62 may include a tapered profile therebetween that further assists the needle assembly 30 in moving smoothly through tissue. The tissue-piercing tip 86 may comprise a substantially flat blade formed of any suitable material that generates little or no MRI artifact and/or is non-conductive or magnetically inert. The tissue-piercing tip 86 may also include tabs or any other suitable coupling means on the proximal portion thereof to aid in the attachment of the tissue-piercing tip 86 to the insert 62.

Referring to FIGS. 4-7, one version of an insert 62 for use with the biopsy device 10 is illustrated. The insert 62 may be provided with a divider 64 adapted to substantially divide the lumen defined by the exterior surface 60 into the cutter lumen 40 and the vacuum lumen 52. The divider 64 may extend longitudinally along the length of the exterior surface 60 such that the cutter lumen 40 and the vacuum lumen 52 are divided into two distinct lumen. In one version, the divider 64 may include, for example, a solid molded polymeric distal end having a flexible web or the like extending proximally that is operably configured to substantially separate the cutter lumen 40 and the vacuum lumen 52 along the entire length of the exterior surface 60. Alternatively, the divider 64, as illustrated, may extend along only a portion of the needle assembly 30 such that the cutter lumen 40 and the vacuum lumen 52 form a single lumen proximally. For example, a reduced length divider 64 may be provided for a device where the cutter only translates through the tissue-receiving port 42 of the needle assembly 30.

The cutter lumen 40 includes a proximal portion and a distal portion. In one version, the cutter lumen 40 forms a passage for receiving the cutter 38 such that it may be actuated proximally and distally therein to sever tissue. An aperture 90 in the insert 62 may be substantially aligned with the tissue-receiving port 42 formed in the exterior surface 60 such that tissue suctioned into the tissue-receiving port 42 may be drawn through the aperture 90 and against the divider 64 prior to being severed. In one version, the insert 62 may be configured to snap into, or otherwise couple with the exterior surface 60, such that the insert 62 may comprise a portion of the tissue-receiving port 42. The tissue-receiving port 42 and aperture 90 may be located adjacent the distal portion of the cutter lumen 40.

In one version, the vacuum lumen 52, located between the divider 64 and the exterior surface 60, includes a proximal portion and a distal portion. The cutter lumen 40 may be oriented above the vacuum lumen 52 with the divider 64 disposed therebetween. A vacuum source (not shown) may be attached to the vacuum lumen 52, possibly at the proximal portion thereof, to provide suction therethrough. Versions herein may reduce the cost and/or time expenditure associated with welding or manufacturing devices having a greater number of components by efficiently dividing the exterior surface 60 into two separate lumen with the insertion of a single component. Reducing the necessary components and providing a more efficient coupling means may ultimately reduce the cost to the patient and/or hospital for such instruments.

The divider 64 of the insert 62 may also include one or more passages, also called interlumen vacuum holes 70, between the cutter lumen 40 and the vacuum lumen 52. When the vacuum source (not shown) is activated, thereby providing suction in the vacuum lumen 52, the interlumen vacuum holes 70 may allow that suction to be communicated into the cutter lumen 40. As best illustrated in FIG. 4, the interlumen vacuum holes 70 may be located between the cutter lumen 40 and the vacuum lumen 52 opposite the tissue-receiving port 42. The insert 62 may further include a cutter stop 72 located in the cutter lumen 40 distal to the tissue-receiving port 42. In one version, the cutter stop 72 aids in severing of the tissue and reduces the potential of tissue fragments becoming lodged in the tip of the insert 62.

Referring, in particular, back to FIG. 3, the insert 62 may be affixed to the exterior surface 60 by any suitable coupling means including, for example, a press fit, an adhesive, or with tabs or detents that mate or the like to form a secure connection. In the illustrated version, the insert 62 is provided with arms 66 extending parallel to the longitudinal axis of the exterior surface 60, the arms 66 having a proximal end and a distal end. At about the distal end of the arms 66, there may be positioned one or a plurality of detents 68 operably configured to mate with one or a plurality of corresponding holes 69 in the exterior surface 60. The detents 68 may be configured with any suitable shape or design such as, for example, an oval or elongated shape that may reduce the probability of shearing during use. During assembly, in one version, the insert 62 may be pushed into the distal end of the exterior surface 60 until the detents 68 engage the holes 69. The arms 66 may be pressed inward slightly upon insertion of the insert 62, such that when the detents 68 reach the holes 69, the arms 66 are biased to push the detents 68 into the holes 69, thereby coupling the two components. In one version, the cutter 38 may be used to insure that the insert 62 remains secured to the exterior surface 60. For example, when the cutter 38 is positioned immediately proximal of the tissue receiving port 42 in preparation for cutting, the cutter 38 may constrain the arms 66 against the exterior surface 60, thereby preventing the detents 68 from disengaging with the holes 69. Versions herein include affixing any suitable insert 62 to the needle assembly 30 by placing the insert 62 into the distal end of the exterior surface 60. Affixing the insert 62 to the exterior surface 60 in a simple two component connection may reduce the cost and/or time expenditure associated with welding or manufacturing a device having a greater number of components. The coupling between the insert 62 and exterior surface 60 may be detachable or permanent. It will be appreciated that versions of the insert 62, the outer surface 60, and the connection therebetween are disclosed by way of example only and are not intended to be limiting in any way. It is contemplated that the insert 62 may have any configuration or design suitable for cooperating with the exterior surface 60 to sample tissue. It is further contemplated that the insert 62 and the exterior surface 60 may be molded as a single integral component.

In operation, the needle assembly 30 may be inserted into a small incision in the body. When utilized, the tissue-piercing tip 86 helps the needle assembly 30 penetrate through tissue until the distal portion 34 of the needle assembly 30 is located adjacent the tissue of interest. The tissue-piercing tip 86 may help to minimize tissue drag experienced during insertion and extraction of the needle assembly 30. Once the needle assembly 30 is properly positioned relative to the tissue of interest, vacuum suction may be applied to the vacuum lumen 52 via the first vacuum line (not shown).

The cutter 38 may have a bore therethrough and may be attached proximally to the second vacuum line (not shown), thereby providing the cutter 38 with axial suction when activated. After a sample has been obtained, and before a second sample is drawn into the tissue-receiving port 42, axial suction, if utilized, may assist the cutter 38 in pulling the tissue sample through the cutter lumen 40 as the cutter 38 is withdrawn. Once the cutter 38 has been withdrawn from the cutter lumen 40, the sample may be cleared from the cutter 38 into, for example, a tissue collection site 46 located on the handle 20 or an adjacent platform. At that point, another sample may be obtained by applying vacuum to draw a sample into the tissue-receiving port 42 and advancing the cutter 38 to sever the sample. This procedure may be repeated until the desired number of samples has been acquired.

The tissue-piercing tip 86 may be formed of a material providing sufficient strength and rigidity to allow it to move through tissue with minimal deflection such as, for example, titanium. In one version, the tissue-piercing tip 86, including the above-described features included thereon, may be stamped or otherwise configured from any suitable material including, for example, MRI compatible and non-conductive resins such as Ultem and Vectra. The tissue-piercing tip 86 may also be formed from ceramics or glass. The cutting edge 92 may be sharpened by any suitable method known in the art. The tissue-piercing tip 86 may be welded to the insert 62. Alternatively, the tissue-piercing tip 86 may be attached to the insert 62 through any suitable method known in the art that provides satisfactory strength of attachment between the tissue-piercing tip 86 and the insert 62 including, but not limited to, adhesive, press-fit, or screws.

The insert 62 material may be selected from materials including, but not limited to, Ultem, Vectra, plastics, thermoplastics, thermoresins, polymers, and/or combinations thereof. Additionally, the insert 62 may be configured from a biomedically implantable or compatible material such that, should small pieces of the insert 62 be sheared by the cutter 38, the pieces will not have a harmful effect on the patient if left therein. For instance, the molded features may be formed of a liquid crystal polymer, a glass reinforced polymer, titanium, and/or polysulfone. One suitable material is a glass reinforced liquid crystal polymer such as VECTRA A130 available from Ticona Corp. In one version, the injected material may have a melt flow index of at least about 10 grams/minute and, more particularly, of at least about 15 grams/minute. In a further version, the molded features may be formed of a high density polyethylene (HDPE) or ultra high molecular weight polyethylene (UHMWPE) used in hip implants or implantable grade polyether-etherketone (PEEK).

Figure 8:
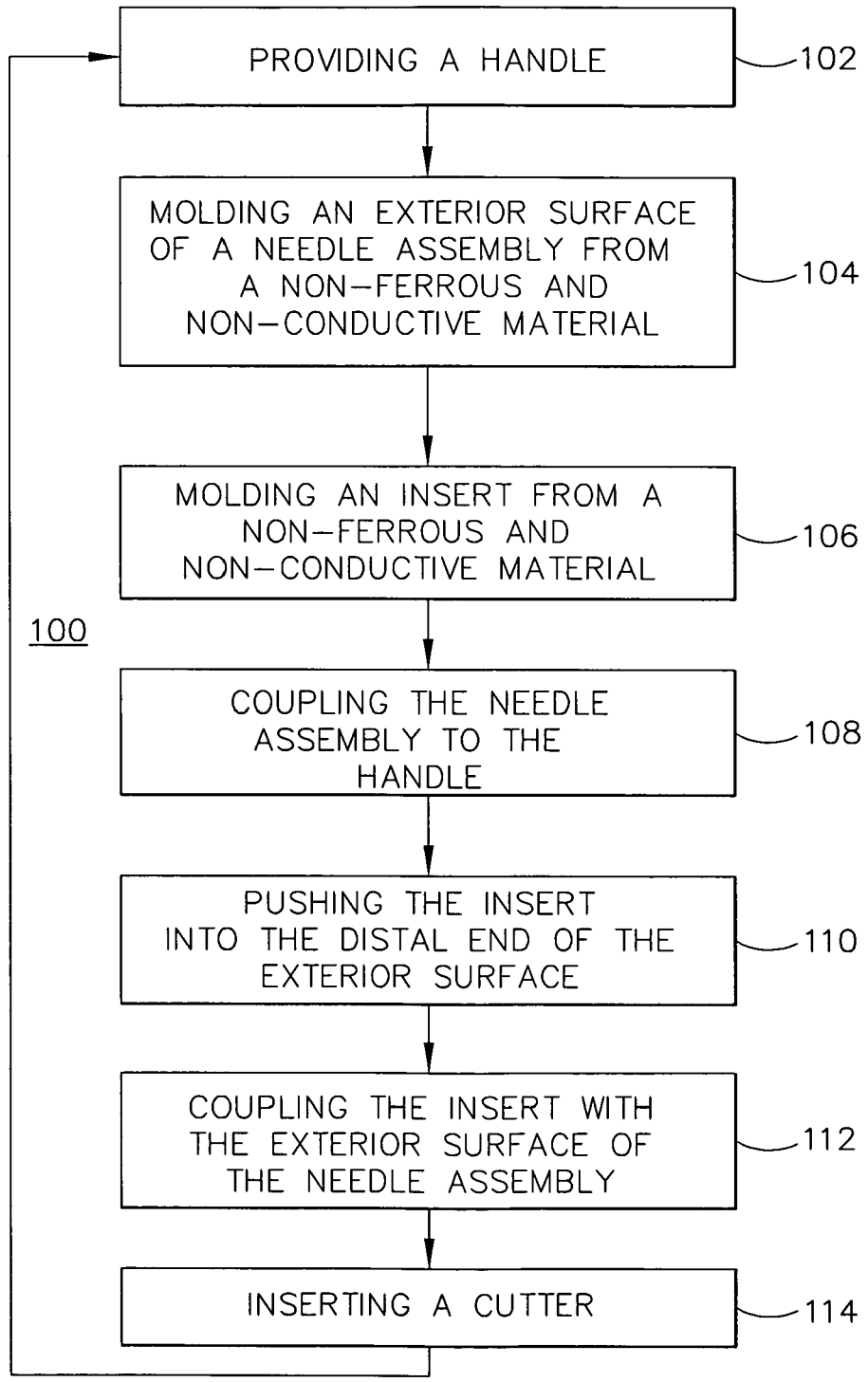
FIG. 8 is a flow chart depicting one version of a method for assembling a biopsy device.

FIG. 8 illustrates one version of a method 100 for assembling a biopsy device. Step 102 of the method 100 includes providing a handle with a longitudinally extendable cutter tube such as, for example, the handle 20 disclosed herein. It will be appreciated that any suitable handle, such as a purely mechanical handle, may be substituted for the handle 20. Step 104 of the method 100 includes molding or otherwise creating an exterior surface 60 from a non-ferrous and/or non-conductive material such as, for example, a carbon composite, a woven carbon composite, Ultem, a high density polyethylene (HDPE), an implantable grade polyether-etherketone (PEEK), and/or Vectra. Step 106 of the method 100 includes molding or otherwise creating an insert 62 from a non-ferrous and/or non-conductive material such as, for example, a polymeric, a carbon composite, a woven carbon composite, Ultem, and/or Vectra. Step 108 of the method 100 includes coupling the needle assembly to the handle, where step 108 may include permanently or detachably coupling the exterior surface 60 to the handle 20. Step 110 of the method 100 includes pushing the insert 62 into, for example, a distal opening in the exterior surface 60. Step 112 includes coupling the exterior surface 60 with the insert 62 by providing a snap fit, by mating corresponding holes and detents located on the exterior surface 60 and the insert 62, by providing an adhesive, and/or by any other suitable connection means. Step 114 includes inserting or otherwise providing the needle assembly 30 with a cutter 38 operably configured to cut tissue samples.

While various versions of the present invention have been shown and described herein, it will be obvious to those skilled in the art that such alternatives are provided by way of example only. Numerous variations, changes, and substitutions will now occur to those skilled in the art without departing from the present invention. Additionally, each component or element may be described in terms of a means for performing the component's function. It will be appreciated that steps discussed in accordance with disclosed methods are not limited to the order in which they are presented in flow charts, in the disclosure, or the like, where any suitable step may be performed at any time or, if desirable, may be eliminated altogether. Accordingly, it is intended that the invention be limited only by the spirit and scope of the appended claims.

What is claimed is:

1. A biopsy device comprising:
   (a) a handle; and
   (b) a needle assembly attached to said handle, wherein said needle assembly comprises:
      (i) an outer member having an exterior surface configured from a non-ferrous and non-conductive material, the outer member having a tissue-receiving aperture and holes formed through the exterior surface, the outer member defining a lumen;
      (ii) an insert configured from a non-ferrous and non-conductive material and attached to said outer member, wherein said insert comprises a divider configured to separate at least a portion of the lumen defined by said outer member into a vacuum lumen and a cutter lumen, wherein said insert further comprises longitudinally extending arms having detents operably configured to engage said holes formed through said exterior surface; and
      (iii) a cutter, wherein said cutter is operably configured to translate within said cutter lumen to sever tissue retained within said tissue receiving aperture, wherein said cutter is further operably configured to maintain the coupling between said insert and said outer member by pressing said insert into said outer member such that said detents are unable to disengage said holes.

2. The biopsy device of claim 1, wherein said exterior surface is configured from a high density polyethylene.

3. The biopsy device of claim 1, wherein said exterior surface is configured from an implantable grade polyether-etherketone.

4. The biopsy device of claim 1, wherein said divider extends along a portion of said exterior surface.

5. The biopsy device of claim 1, wherein said insert is coupled with said exterior surface by pushing said insert into a distal end of said outer member.

6. The biopsy device of claim 5, wherein said insert is constructed from a material selected from the group consisting of a high density polyethylene and an implantable grade polyether-etherketone.

7. A biopsy device comprising:
   (a) a handle; and
   (b) a needle assembly attached to said handle, wherein said needle assembly comprises:
      (i) an outer member having an exterior surface configured from a non-ferrous and non-conductive material selected from the group consisting of a glass reinforced liquid crystal polymer, and a polyetherimide, where said outer member further includes a tissue-receiving aperture located at a distal end thereof, the outer member defining a lumen;
      (ii) an insert constructed from a non-ferrous and non-conductive material and attached to said outer member, wherein said insert includes a divider configured to divide at least a portion of the lumen defined by said outer member into a vacuum lumen and a cutter lumen, where said insert is coupled with said outer member by pushing said insert into the distal end of said outer member, where said insert further comprises longitudinally extending arms having detents thereon operably configured to engage corresponding holes formed through said exterior surface such that engaging said detents and said corresponding holes permanently couples said insert and said outer member; and
      (iii) a cutter, wherein said cutter is operably configured to translate within said cutter lumen to sever tissue retained within said tissue receiving aperture, wherein said cutter presses said insert into said outer member such that said detents engage said corresponding holes.

* * * * *